United States Patent
Porcheron et al.

(10) Patent No.: US 9,132,375 B2
(45) Date of Patent: Sep. 15, 2015

(54) SHAPING CAPTURE MASSES FOR THE PURIFICATION OF A LIQUID OR GAS FEED CONTAINING HEAVY METALS

(75) Inventors: Fabien Porcheron, Rueil Malmaison (FR); Karin Barthelet, Lyons (FR); Arnaud Baudot, Vernaison (FR); Antoine Daudin, Corbas (FR); Jean-Marc Schweitzer, Villette de Vienne (FR); Jeremy Gazarian, Condrieu (FR)

(73) Assignee: IFP ENERGIES NOUVELLES, Rueil-Malmaison Cedex (FR)

(*) Notice: Subject to any disclaimer, the term of this patent is extended or adjusted under 35 U.S.C. 154(b) by 0 days.

(21) Appl. No.: 14/349,728

(22) PCT Filed: Sep. 12, 2012

(86) PCT No.: PCT/FR2012/000362
§ 371 (c)(1),
(2), (4) Date: Jun. 27, 2014

(87) PCT Pub. No.: WO2013/050668
PCT Pub. Date: Apr. 11, 2013

(65) Prior Publication Data
US 2014/0308189 A1 Oct. 16, 2014

(30) Foreign Application Priority Data
Oct. 4, 2011 (FR) .................................. 11 03015

(51) Int. Cl.
*B01D 53/04* (2006.01)
*C07C 7/12* (2006.01)
(Continued)

(52) U.S. Cl.
CPC ............. *B01D 53/04* (2013.01); *B01D 53/02* (2013.01); *B01D 53/64* (2013.01); *B01J 20/0237* (2013.01);
(Continued)

(58) Field of Classification Search
CPC ............. B01D 53/64; B01D 2253/104; B01D 2253/1128; B01D 2253/34; B01D 2257/602; B01D 15/00; C07C 7/12; B01J 20/08; B01J 20/28004; B01J 20/28014; B01J 2219/30223; B01J 2219/30242; B01J 2219/30296; B01J 2219/30475; B01J 2219/3188
USPC ....................................... 502/527.11, 527.24
See application file for complete search history.

(56) References Cited

U.S. PATENT DOCUMENTS
3,966,644 A 6/1976 Gustafson et al.
4,673,664 A 6/1987 Bambrick et al.
(Continued)

FOREIGN PATENT DOCUMENTS
EP 0218147 A1 4/1987
FR 2615756 A1 * 12/1988 ............. B01D 53/64
(Continued)

OTHER PUBLICATIONS
International Search Report for PCT/FR2012/000362 dated Nov. 7, 2012.
(Continued)

*Primary Examiner* — Timothy Vanoy
(74) *Attorney, Agent, or Firm* — Millen White Zelano & Branigan, P.C.

(57) ABSTRACT

A process for the elimination of heavy metals, in particular mercury and possibly arsenic and lead, present in a gaseous or liquid effluent by means of a fixed bed process using an adsorbent in the form of monolithic or supported extrudates, said extrudates being characterized by a length h and a section comprising at least three lobes. The adsorbent is composed of at least one active phase based on sulphur in the elemental form or in the form of a metallic sulphide. The process is advantageously applicable to the treatment of gas of industrial origin, synthesis gas, natural gas, gas phase condensates and liquid hydrocarbon feeds.

13 Claims, 3 Drawing Sheets

(51) Int. Cl.
  *B01J 20/08* (2006.01)
  *B01D 53/02* (2006.01)
  *B01J 20/30* (2006.01)
  *B01D 53/64* (2006.01)
  *B01J 20/28* (2006.01)
  *B01J 20/02* (2006.01)

(52) U.S. Cl.
  CPC .......... *B01J 20/0266* (2013.01); *B01J 20/0285* (2013.01); *B01J 20/08* (2013.01); *B01J 20/28004* (2013.01); *B01J 20/28016* (2013.01); *B01J 20/28057* (2013.01); *B01J 20/3007* (2013.01); *C07C 7/12* (2013.01); *B01D 2253/104* (2013.01); *B01D 2253/1128* (2013.01); *B01D 2257/602* (2013.01); *B01D 2259/401* (2013.01); *B01J 2219/30223* (2013.01); *B01J 2219/30242* (2013.01); *B01J 2219/30416* (2013.01); *B01J 2219/30475* (2013.01)

(56) References Cited

U.S. PATENT DOCUMENTS

| | | | |
|---|---|---|---|
| 6,214,765 B1 * | 4/2001 | Fromson et al. | 502/355 |
| 6,624,114 B1 * | 9/2003 | Eberle et al. | 502/439 |
| 8,993,473 B2 * | 3/2015 | Melde et al. | 502/209 |
| 2009/0115077 A1 * | 5/2009 | Niknafs et al. | 261/94 |
| 2009/0306410 A1 * | 12/2009 | Brandstadter et al. | 549/262 |
| 2011/0226700 A1 | 9/2011 | Hetherington et al. | |
| 2013/0053234 A1 | 2/2013 | Fish et al. | |
| 2013/0204065 A1 * | 8/2013 | Kanazirev et al. | 585/824 |

FOREIGN PATENT DOCUMENTS

| | | |
|---|---|---|
| WO | 2010061212 A1 | 6/2010 |
| WO | 2011021024 A1 | 2/2011 |

OTHER PUBLICATIONS

Duffus, J. H. et al., "Heavy Metals—a meaningless term?" Pure & Applied Chemistry, Jan. 1, 2002, vol. 74, No. 5, pp. 793-807.

* cited by examiner

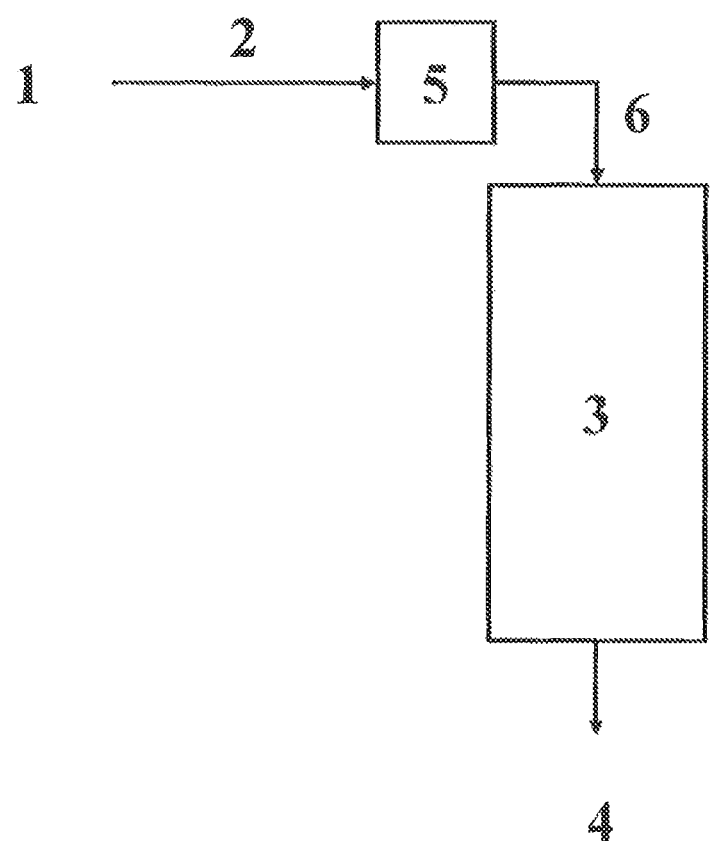

SHAPING CAPTURE MASSES FOR THE PURIFICATION OF A LIQUID OR GAS FEED CONTAINING HEAVY METALS

FIELD OF THE INVENTION

The present invention relates to the elimination of heavy metals such as mercury, arsenic or lead, present in a gaseous or liquid effluent by means of a fixed bed process using an adsorbent in the form of monolithic or supported extrudates as defined below and comprising at least one active phase based on sulphur in the elemental form or in the form of a metallic sulphide. The invention is advantageously applicable to the treatment of gas of industrial origin, synthesis gas, natural gas, gas phase condensates and liquid hydrocarbon feeds.

PRIOR ART

Mercury is a metallic contaminant which is found in gaseous or liquid hydrocarbons produced in many regions of the world, such as the Gulf of Niger, South America or North Africa.

Eliminating mercury from hydrocarbon cuts is desirable industrially for several reasons: the safety of the operators, since elemental mercury is volatile and presents serious risks of neurotoxicity by inhalation while its organic forms present similar risks by skin contact; and also for reasons of preventing the deactivation of heterogeneous catalysts used to upgrade such liquid hydrocarbon cuts, since mercury amalgamates very easily with noble metals such as platinum or palladium which are used in the form of nanoparticles dispersed on porous supports that can be used in catalytic operations as diverse as the selective hydrogenation of olefins produced by steam cracking or catalytic cracking of liquid hydrocarbons.

Industrially, the elimination of heavy metals, in particular mercury, from liquid or gaseous hydrocarbon cuts is carried out by allowing them to move through beds of capture masses. The term "capture mass" or "adsorbent" as used in the present invention means any type of solid in the monolithic or supported form containing, within it or on its surface, an active element that is capable of reacting irreversibly with an impurity, such as mercury, contained in the feed to be purified. This elimination of mercury from liquid or gaseous hydrocarbon cuts is generally carried out by moving the effluent to be treated through beds of adsorbents containing an active phase that can react with the mercury. The skilled person will be aware that the capture of mercury may be carried out easily by reacting it with an active phase based on sulphur or a sulphur-containing compound, in particular metallic sulphides, the mercury then forming an amalgam with the sulphur to form the chemical species HgS known as cinnabar or mercuric sulphide. As an example, U.S. Pat. No. 7,645,306 B2 demonstrates that cuprous copper sulphide, CuS, reacts irreversibly with elemental mercury in the following manner:

$$Hg^0 + 2CuS \rightarrow Cu_2S + HgS \quad (1)$$

U.S. Pat. No. 5 053 209 demonstrates that sulphur reacts reversibly with elemental mercury in the following manner:

$$2Hg^0 + S_2 \leftrightarrow 2HgS \quad (2)$$

Martellaro et al (Environmental application of mineral sulphides for removal of gas-phase Hg(0) and aqueous Hg2: Separation Science and Technology, 2001, 36, 1183-1196) have also demonstrated that gold sulphide can react with elemental mercury in the following manner:

$$Au_2S + Hg^0 \rightarrow 2Au^0 + HgS \quad (3)$$

These reactions are specific in that the product or products formed that contain mercury are insoluble in the effluent to be purified, and thus can be used to extract heavy metals such as mercury from the effluent, thereby avoiding such disadvantages as those described above.

These various chemical reactions are generally carried out in a process by bringing the effluent to be treated into contact with an adsorbent (also known as a capture mass) which is either monolithic, in which the particles of active phase may be bonded together via binders, or supported, in which the active phase is dispersed within or on the surface of a porous solid support.

Industrially, the elimination of mercury from liquid or gaseous hydrocarbon cuts is generally carried out by allowing them to move through beds of adsorbents. The effluent is thus cleansed of heavy metals such as mercury, which remains trapped in the bed of adsorbent or capture mass. The adsorbent used is generally regenerated in the process under consideration. As an example, application US 2008/0041227 describes the use of a process in which at least two beds of adsorbent are used successively in adsorption mode then in regeneration mode. In adsorption mode, the bed of adsorbents in which a stream of natural gas moves captures at least mercury and water. When that bed of adsorbents approaches saturation, the bed is taken off line and switched into a regenerative mode in which a heated stream of regenerative gas is passed through in order to remove the mercury and the water.

However, that type of regenerative process suffers from disadvantages from a cost viewpoint as it involves employing and operating a plurality of beds of adsorbent in parallel and the complex management of a plurality of gas streams containing mercury. Another major problem in heavy metal capture processes, in particular for capturing mercury, is that the quantity of mercury that an adsorbent can receive is limited by its saturation capacity, i.e. the total quantity of mercury which can react with the active phase present in the adsorbent. It is well known to the skilled person that it is not favourable to reach that saturation capacity in the process, as the efficiency of the adsorbent approaching those conditions is greatly reduced, in the sense that large quantities of mercury are no longer captured by the active phase.

Processes for the purification of heavy metals are thus constrained to maintain extremely high levels of efficiency for as long a period as possible, in order to reduce the frequency of replacement of the capture mass employed as much as possible.

Frequently, the performance of a capture mass in a process for eliminating heavy metals such as mercury is characterized by the dynamic capacity of the bed of capture mass, i.e. its capacity to maintain a maximum level of performance for as long an operational period as possible. This performance is defined by the efficiency, E, in accordance with the formula:

$$E(\%) = [([Hg]_0 - [Hg]_S)/[Hg]_0] \times 100 \quad (4)$$

where $[Hg]_S$ is the concentration of mercury in the effluent at the outlet from the bed and $[Hg]_0$ is the concentration of mercury in the effluent at the inlet to the bed.

Adsorbents are usually shaped using methods which are known to the skilled person, in particular mixing-extrusion, pelletization, granulation, oil-drop methods, etc. The adsorbents may thus be in the shape of beads, cylinders, cart wheels, hollow cylinders, honeycombs or any other geometric shape used by the skilled person. The skilled person will be well aware that this step for shaping the capture mass has an effect on the pressure drop occurring during passage of the gaseous effluent through the fixed bed. It is advantageous to minimize the pressure drop during passage through the bed of capture mass, as this pressure drop has to be compensated for by compressing the gaseous effluent, which involves substantial investment costs and operational costs.

However, there is no information concerning any influences of the shape of the adsorbent on the dynamic capacity of a bed of capture mass used to purify an effluent containing heavy metals, in particular mercury. Thus, a priori, the shape of an adsorbent, for the same structural and textural properties, has no influence on the adsorption performance of the process.

However, surprisingly, the Applicant has discovered that using an adsorbent in the form of monolithic or supported extrudates means that the shape of an extrudate characterized by a length h and a section comprising at least three lobes in accordance with the invention means that improved adsorption performances can be obtained in that the dynamic capacity is larger than that of adsorbents in the form of beads or in the form of extrudates with other geometries.

The use of such capture masses in a purification process is of major interest and advantage in all processes for the treatment of gaseous or liquid effluents for the elimination of heavy metals present in these feeds.

SUMMARY OF THE INVENTION

The present invention concerns a fixed bed process for the elimination of heavy metals, in particular mercury, arsenic and lead, contained in a gaseous or liquid effluent, by bringing the effluent into contact with a capture mass in the form of a monolithic or supported extrudate comprising an active phase containing at least sulphur in the elemental form or cuprous copper sulphide, CuS, or the metallic sulphide $FeS_2$, said extrudate being characterized by a length h in the range 0.5 to 100 mm and a section comprising at least three lobes.

The Applicant has discovered that carrying out the process of the invention can result in large dynamic capacities. Carrying out the process of the invention means that for the same quantity of active phase, more heavy metals can be captured from a gaseous or liquid feed and thus the feed to be treated can be purified more effectively. More precisely, carrying out the process of the invention has the advantage of a higher efficiency in the adsorption of heavy metals, advantageously mercury, for the same operational period, or in other words a longer operational period while maintaining an adsorption efficiency beyond a given threshold compared with prior art adsorbents. The process of the invention also offers the advantage of reducing investment costs because a smaller volume of adsorbents can be used to treat a gaseous or liquid feed containing heavy metals.

Other characteristics and advantages of the invention will be better understood and will become apparent from the following description.

DETAILED DESCRIPTION OF THE INVENTION

The invention concerns a fixed bed process for the elimination of heavy metals, in particular mercury, arsenic and lead, contained in a gaseous or liquid effluent, by bringing the effluent into contact with a capture mass in the form of a monolithic or supported extrudate comprising an active phase containing at least sulphur in the elemental form or cuprous copper sulphide, CuS, or the metallic sulphide $FeS_2$, said extrudate being characterized by a length h in the range 0.5 to 100 mm and a section comprising at least three lobes.

The section of the extrudate may be characterized by a radius R which satisfies equation (1):

$$R = \cos\theta \cdot (R_0 - r) + \sqrt{\cos^2\theta \cdot (R_0 - r)^2 - R_0 \cdot (R_0 - 2 \cdot r)} \quad (1)$$

where $$\theta = \alpha - k \cdot \frac{2 \cdot \pi}{n}$$

and $$k = \mathrm{int}\left(\frac{|\alpha + \frac{\pi}{2}|}{\frac{2 \cdot \pi}{n}}\right)$$

and $$\alpha \in [0, 2\pi]$$

where $R_0$ represents the maximum distance between the centre of the extrudate and the wall of the extrudate, R represents the distance between the centre of the extrudate and the wall of the extrudate for an angle α, r represents the radius of one lobe of the extrudate, and n corresponds to the number of lobes of the extrudate, and the function Int( ) represents the integral part of the ratio $$\left(\frac{|\alpha + \frac{\pi}{2}|}{\frac{2 \cdot \pi}{n}}\right) \text{ and } |\alpha + \frac{\pi}{2}|$$

represents the absolute value of the sum $$\alpha + \frac{\pi}{2}$$

In the present invention, the term "function Int( )" means the integral part of the ratio $$\left(\frac{|\alpha + \frac{\pi}{2}|}{\frac{2 \cdot \pi}{n}}\right)$$

Thus, by way of illustration, application of the function Int( ) to a ratio equal to 1.8 corresponds to an integral value 1, i.e. Int(1.8)=1, and application of the function Int( ) to a ratio equal to 2.1 corresponds to an integral value 2, i.e. Int(2.1)=2.

Advantageously, in accordance with the invention, the number of lobes of the extrudate n is selected from the group constituted by the integral values 3, 4, 5, 6, 7, 8, 9 and 10; preferably, the number of lobes n is selected from the group constituted by the integral values 3, 4, 5 and 6; more preferably, the number of lobes n is selected from the group constituted by the integral values 3 and 4; and highly preferably, the number of lobes n is 3.

For greater clarity in the application of equation (1) of the invention, FIG. 1 shows a non-limiting diagrammatic illustration of a section of an extrudate in which all of the parameters $R_0$, R, r and α are shown, n being the number of lobes of the extrudate. The section of the extrudate corresponds to a section of the extrudate in a plane perpendicular to the direction of extrusion. FIG. 1 can be seen to have an extrudate section comprising four lobes.

BRIEF DESCRIPTION OF DRAWINGS

FIG. 3 shows another embodiment of the steps of the invention.

Figure 1:
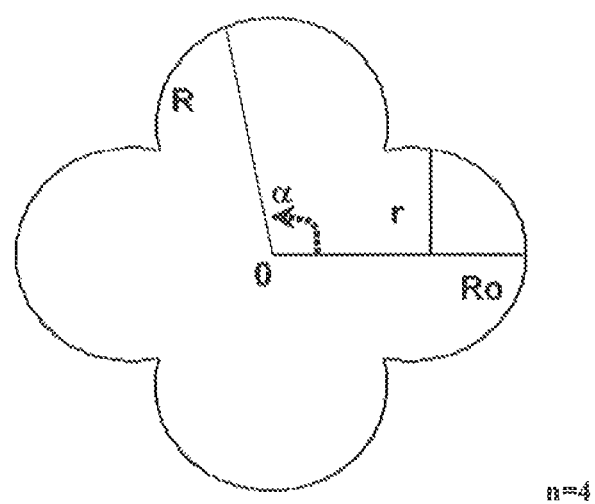
FIG. 1 shows a non-limiting diagrammatic illustration of a section of an extrudate in which all of the parameters $R_0$, R, r and α are shown, n being the number of lobes of the extrudate.

Processes for the manufacture of monolithic or supported extrudates which are known to the skilled person usually cause imperfections in the shape linked to the mechanics of the phases present, which may give rise to a difference between the measurable value R ($R_{mes}$) and the value R defined by equation (1). The measurable value R ($R_{mes}$) linked to the value R defined by equation (1) of the present invention is advantageously in the range R−15% R to R+15% R, preferably in the range R−10% R to R+10% R, more preferably in the range R−5% R to R+5% R, and more preferably in the range R−3% R to R+3% R.

In a variation of the process of the invention, the adsorbent of the invention comprises a pre-active phase that may be activated subsequently. In another variation of the process of the invention, said adsorbent comprises a mixture of active phase and pre-active phase.

In the context of the present invention, the active phase corresponds to sulphur present in the form of elemental sulphur, or to cuprous copper sulphide, CuS, or to iron sulphide, $FeS_2$. Preferably, at least 90% by weight, or even 95% by weight or 98% by weight of the active phase is composed of elemental sulphur, or of cuprous copper sulphide, CuS, or of iron sulphide, $FeS_2$. Preferably, the active phase is composed of cuprous copper sulphide, CuS.

In a variation of the invention, the active phase of the invention may also be composed of a mixture of sulphur in the elemental form and of sulphur in the form of cuprous copper sulphide, CuS.

Advantageously, the active phase of the adsorbent of the invention comprises in the range 1% to 70% by weight of sulphur with respect to the total weight of the capture mass, preferably in the range 2% to 25% and more preferably in the range 3% to 20%.

In the context of the present invention, the "pre-active phase" is intended to mean the phase of the adsorbent containing the metal M in the metallic oxide form where the metal M is selected from the group constituted by copper and iron. Highly preferably, the metal used is copper. Preferably, the metallic oxide used is copper oxide or copper hydrogen carbonate or copper sulphate or copper acetate; more preferably, the metallic oxide is copper oxide. Preferably, the metallic oxide used is iron(II), ferrous, oxide, FeO, or iron(III), ferric, oxide, $Fe_2O_3$ or iron(II,III) oxide, $Fe_3O_4$. Highly preferably, the metallic oxide is iron(III) oxide, ferric oxide, $Fe_2O_3$.

The proportion by weight of metal with respect to the total weight of the capture mass of the invention is in the range 1% to 60%, preferably in the range 2% to 40%, more preferably in the range 5% to 30%, highly preferably in the range 5% to 20%.

When a pre-active phase is used, the process of the invention comprises a sulphurization step consisting of transforming all or at least a portion of the pre-active phase into the form of a metallic oxide as defined in the invention into an active sulphurized phase as defined above. Said sulphurization step may be carried out in-situ, i.e. during a process used in accordance with the invention to eliminate heavy metals such as mercury. In this latter case, it is necessary to provide a sulphur-containing element in the feed to be treated. The sulphurization step may also be carried out ex-situ, i.e. the sulphurization step is carried out before using the adsorbent (or capture mass) in the elimination process of the invention. The fact that the sulphurization step is carried out means that the sulphide forms CuS or $FeS_2$ are obtained; they react best with the mercury. Thus, the capture mass obtained after the sulphurization step is used directly to capture heavy metals contained in a feed, without undergoing a complementary reduction step.

In the case in which the adsorbent employed in accordance with the invention is composed of a porous support, the porous support may be selected irrespectively from the alumina, silica-alumina, silica, zeolite and activated charcoal families. In this case, the active phase is deposited onto the porous support. Advantageously, the porous support is based on alumina or on activated charcoal. In a preferred variation of the invention, the porous support is at least constituted by alumina obtained by the gel method, also termed a gel alumina in the present invention. These aluminas may be obtained using any synthesis method which is known to the skilled person, in particular by precipitation by bringing an aqueous solution of acid salts into contact with an alkaline solution of aluminium salts or a mixture of the two types of salts. Preferably, the porous support is constituted by alumina that has at least been obtained from an aluminium oxy(hydroxide) or gamma aluminium oxy(hydroxide) or delta aluminium oxy(hydroxide).

In a preferred variation, the support for the capture mass of the invention is constituted by at least 50% by weight of gamma alumina, preferably at least 99% of gamma alumina. In another variation of the invention, the porous support for the capture mass is constituted by at least 50% by weight of delta alumina, preferably 80% delta alumina. In a more preferred variation, the porous support for the capture mass of the invention is constituted by 100% alumina gel, preferably obtained from a precursor of the aluminium oxy(hydroxide) type, characterized by a specific surface area in the range 150 to 600 $m^2/g$, preferably in the range 200 to 400 $m^2/g$, more preferably in the range 150 to 320 $m^2/g$.

The adsorbents of the invention are shaped using means that are known to the skilled person, preferably by mixing-extrusion.

Preferably, the adsorbents of the invention are in the form of monolithic or supported extrudates with a diameter that is generally in the range 0.5 to 100 mm, preferably in the range 0.5 to 50 mm, preferably in the range 0.5 to 10 mm.

Preferably, the adsorbents of the invention are in the form of monolithic or supported extrudates with a length h that is generally in the range 0.5 to 100 mm, preferably in the range 0.5 to 50 mm, more preferably in the range 0.5 to 30 mm and highly preferably in the range 0.5 to 10 mm.

The adsorbents of the invention may be used to purify gaseous or liquid effluents containing heavy metals. Examples which may be cited are combustion fumes, synthesis gas or natural gas, liquid cuts of natural gas, oil, oil cuts, or petrochemicals intermediates.

The process of the invention may be carried out using any method known to the skilled person. By way of non-limiting indication, the process of the invention may be carried out in accordance with various steps, referring to FIG. 2 or FIG. 3.

Figure 2:
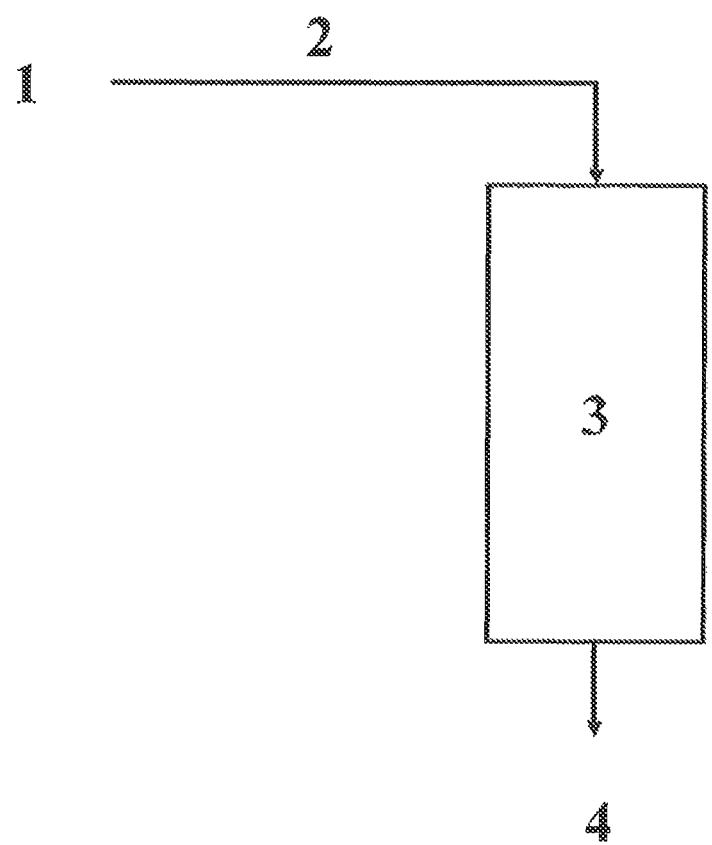
FIG. 2 shows one embodiment of the steps of the invention.

In a first variation, the process of the invention comprises various steps; referring to FIG. 2, a liquid or gaseous feed 1, containing heavy metals such as mercury, as or lead, is introduced via a line 2 into a bed containing the capture mass 3 of the invention. The bed of capture mass adsorbs the heavy metals, preferably mercury contained in the feed so as to obtain, at the outlet from said bed, a cleansed effluent 4, i.e. the concentration of heavy metals in the effluent at the outlet from the fixed bed is less than the concentration of heavy metals in the feed at the inlet to the capture mass bed.

In a second variation, the process of the invention comprises the various steps referred to in FIG. 3, namely that a liquid or gaseous feed 1 containing heavy metals is introduced via a line 2 into a drier 5 allowing water to be extracted from said feed. The effluent obtained at the outlet from the drier is then introduced via a line 6 into a bed of capture mass 3 of the invention. The bed of capture mass adsorbs the heavy metals, preferably mercury contained in the feed so as to obtain a purified effluent 4 at the outlet from said bed, i.e. the concentration of heavy metals in the effluent at the outlet from the fixed bed is lower than the concentration of heavy metals in the effluent at the inlet to the bed of capture mass.

The feed for the process of the invention generally corresponds to gaseous or liquid effluents containing heavy metals such as mercury, arsenic or lead. Examples that may be cited are combustion fumes produced by the combustion of hydrocarbons, biogas, and coal in a boiler or by a gas turbine, for example with the aim of producing electricity. These fumes are at a temperature in the range 20° C. to 60° C., a pressure in the range 1 to 5 bars (1 bar=0.1 MPa) and may comprise in the range 50% to 80% of nitrogen, in the range 5% to 40% of carbon dioxide, in the range 1% to 20% of oxygen and a few impurities such as SOx and NOx, if they are not eliminated downstream of the deacidification process. Synthesis gas containing carbon monoxide CO, hydrogen $H_2$ (generally in a $H_2/CO$ ratio of close to 2), steam (generally saturated at the temperature at which washing is carried out) and carbon dioxide $CO_2$ (of the order of ten percent) may also be cited. The pressure of the feed is generally in the range 2 to 3 MPa, but may reach 7 MPa. The feed may also contain sulphur-containing impurities ($H_2S$, COS, etc), nitrogen-containing impurities ($NH_3$, HCN) and halogen-containing impurities.

The feed of the invention may also comprise natural gas, mainly constituted by gaseous hydrocarbons, but may also contain several of the following acidic compounds: $CO_2$, $H_2S$, mercaptans, COS, $CS_2$. The quantity of these acidic compounds is highly variable and may be up to 40% for $CO_2$ and $H_2S$. The temperature of the natural gas may be in the range 20° C. to 100° C., and the pressure of the natural gas to be treated is advantageously in the range 1 to 12 MPa.

The feed for the invention contains heavy metals in varying proportions. In general, the feed of the invention comprises mercury, arsenic, lead, vanadium and cadmium, preferably mercury, arsenic, lead, preferably mercury and arsenic, and more preferably mercury. Advantageously, in the case of a natural gas effluent, it contains in the range 10 nanograms to 1 gram of mercury per $Nm^3$ of gas. The feed to be treated in accordance with the invention may also contain water in varying proportions. The humidity in the gaseous effluents is advantageously in the range 0 to 100%, preferably in the range 0 to 99% and more preferably in the range 0 to 90%.

In all cases, the feed to be treated in accordance with the invention contains heavy metals in different forms. As an example, mercury is present in a form known as Hg(0), corresponding to elemental or atomic mercury, in the molecular form, or in the ionic form, for example $Hg^{2+}$ and its complexes.

The temperature of the feed to be treated is generally in the range −50° C. to +200° C., preferably in the range 0° C. to 150° C. and highly preferably in the range 20° C. to 100° C., preferably in the range 30° C. to 75° C. The pressure of the feed to be treated may be in the range 1 to 50 MPa, preferably in the range 1 to 40 MPa, more preferably in the range 5 to 40 MPa, still more preferably in the range 10 to 35 MPa and highly preferably in the range 15 to 30 MPa.

Preferably, the process of the invention is carried out with an HSV (volume of feed per volume of capture mass per hour) in the range 500 to 50000 $h^{-1}$, preferably in the range 1000 to 40000 $h^{-1}$, more preferably in the range 2000 to 30000 $h^{-1}$. Preferably, in the case of a gas feed, the HSV is in the range 4000 to 20000 $h^{-1}$. Preferably, in the case of a liquid feed, the HSV is in the range 0.1 to 50 $h^{-1}$.

The following examples serve to illustrate the invention, but are not in any way limiting.

EXAMPLES

Example A

Preparation of an Adsorbent Based on CuS, M1, in Accordance with the Invention

An adsorbent M1 in accordance with the invention was prepared using a porous alumina support in the form of an extrudate satisfying equation (1) where n=3, which had an active phase based on CuS in a concentration of 4.7% by weight (weight) of sulphur. The trilobe extrudate had a diameter of 1.6 mm and a length of 4 mm.

Example B

Preparation of an Adsorbent Based on CuS, M2 (Comparative)

An adsorbent M2 was prepared using a porous alumina support identical to that used in Example A, in the form of a cylindrical extrudate which had an active phase based on CuS in a concentration of 4.7% by weight of sulphur. The cylindrical extrudate had a diameter of 1.6 mm and a length of 4 mm.

Example C

Preparation of an Adsorbent Based on CuS, M3 (Comparative)

An adsorbent M3 was prepared using a porous alumina support identical to that used in Example A, in the form of a bead which had an active phase based on CuS in a concentration of 4.7% by weight of sulphur. The bead had a diameter of 3 mm.

Example D

Preparation of an Adsorbent Based on S, M4, in Accordance with the Invention

An adsorbent M4 in accordance with the invention was prepared using a porous alumina support in the form of an extrudate satisfying equation (1) where n=3, which had an active phase based on S in a concentration of 4.7% by weight of sulphur. The trilobe extrudate had a diameter of 1.6 mm and a length of 4 mm.

Example E

Preparation of an Adsorbent Based on S, M5 (Comparative)

An adsorbent M5 was prepared using a porous alumina support identical to that used in Example A, in the form of a cylindrical extrudate which had an active phase based on S in a concentration of 4.7% by weight of sulphur. The cylindrical extrudate had a diameter of 1.6 mm and a length of 4 mm.

Example F

Preparation of an Adsorbent Based on S, M6 (Comparative)

An adsorbent M6 was prepared using a porous alumina support identical to that used in Example A, in the form of a bead which had an active phase based on S in a concentration of 4.7% by weight of sulphur. The bead had a diameter of 3 mm.

Example G

Mercury Elimination Tests on Capture Masses M1, M2, M3, M4, M5 and M6

The mercury adsorption performances of the capture masses as prepared were tested in a fixed bed apparatus. A volume $V_m = 18$ cm$^3$ of adsorbents was prepared in a fixed bed configuration. A gaseous stream of nitrogen containing mercury in the following concentration: $[Hg]_e = 1060$ μg·Nm$^{-3}$ of mercury, was passed through the bed of adsorbents at a flow rate of 300 Nl/h (HSV=1666 h$^{-1}$), a temperature of 50° C. and a pressure of 20 MPa. The pressure drop, defined as the difference between the pressure of the gas stream at the outlet from and at the inlet to the reactor, was identical for all tests.

The performance is defined by the efficiency E as follows:

$$E(\%) = [([Hg]_0 - [Hg]_s)/[Hg]_0] \times 100$$

where $[Hg]_s$ is the concentration of mercury in the effluent at the outlet from the bed and $[Hg]_0$ is the concentration of mercury in the effluent at the inlet to the bed.

The performances of the capture masses were compared at the same relative times $\tau = t/t_f$, defined as the ratio at time $t_f$ for which the relationship $[Hg]_s = 0.1 \times [Hg]_0$ is obtained.

| Capture mass | Active phase | Support | Geometry | E/% $\tau = 0.1$ | $\tau = 0.2$ | $\tau = 0.4$ | $\tau = 0.6$ | $\tau = 0.8$ |
|---|---|---|---|---|---|---|---|---|
| M1 (invention) | CuS | Al$_2$O$_3$ | Equation (1), n = 3 | 99.996 | 99.990 | 99.946 | 99.696 | 98.234 |
| M2 (comparative) | CuS | Al$_2$O$_3$ | Cylinder | 99.983 | 99.958 | 99.809 | 99.277 | 97.208 |
| M3 (comparative) | CuS | Al$_2$O$_3$ | Bead | 99.792 | 99.634 | 99.033 | 97.734 | 95.072 |
| M4 (invention) | S | Al$_2$O$_3$ | Equation (1), n = 3 | 100.000 | 99.999 | 99.987 | 99.877 | 98.854 |
| M5 (comparative) | S | Al$_2$O$_3$ | Cylinder | 99.993 | 99.986 | 99.925 | 99.614 | 97.964 |
| M6 (comparative) | S | Al$_2$O$_3$ | Bead | 99.953 | 99.921 | 99.743 | 99.088 | 97.000 |

The performances of the capture masses may also be expressed with respect to the same mercury absorption efficiency. Thus, the maximum time for using the process during which this efficiency is guaranteed by the bed of adsorbent can be compared.

| Capture mass | Active phase | Support | Geometry | $\tau$ E = 99.9% | E = 99.7% | E = 99.5% | E = 99.3% | E = 99.1% | E = 99.0% |
|---|---|---|---|---|---|---|---|---|---|
| M1 (invention) | CuS | Al$_2$O$_3$ | Equation (1), n = 3 | 0.473 | 0.598 | 0.654 | 0.692 | 0.723 | 0.736 |
| M2 (comparative) | CuS | Al$_2$O$_3$ | Cylinder | 0.309 | 0.468 | 0.545 | 0.598 | 0.633 | 0.647 |
| M3 (comparative) | CuS | Al$_2$O$_3$ | Bead | 0.004 | 0.161 | 0.259 | 0.327 | 0.384 | 0.406 |
| M4 (invention) | S | Al$_2$O$_3$ | Equation (1), n = 3 | 0.581 | 0.677 | 0.723 | 0.755 | 0.774 | 0.787 |
| M5 (comparative) | S | Al$_2$O$_3$ | Cylinder | 0.435 | 0.564 | 0.628 | 0.673 | 0.701 | 0.714 |
| M6 (comparative) | S | Al$_2$O$_3$ | Bead | 0.244 | 0.424 | 0.511 | 0.561 | 0.604 | 0.619 |

The above examples illustrate the ability of the adsorbents of the invention to offer greater mercury adsorption efficiencies for the same operational period or for longer operational periods, meaning that mercury adsorption efficiency can be maintained beyond a given threshold compared with prior art adsorbents.

The invention claimed is:

1. A fixed bed process for the elimination of heavy metals contained in a gaseous or liquid effluent, comprising bringing the effluent into contact with a capture mass in the form of a monolithic or supported extrudate comprising an active phase containing at least sulphur in the elemental form or cuprous copper sulphide, CuS, or the metallic sulphide $FeS_2$, said extrudate being characterized by a length h in the range 0.5 to 100 mm and a section comprising at least three lobes.

2. A process according to claim 1, in which the section of the extrudate is characterized by a radius R satisfying equation (1):

$$R = \cos\theta \cdot (R_0 - r) + \sqrt{\cos^2\theta \cdot (R_0 - r)^2 - R_0 \cdot (R_0 - 2 \cdot r)} \quad (1)$$

where $$\theta = \alpha - k \cdot \frac{2 \cdot \pi}{n}$$

and $$k = \text{int}\left(\frac{\left|\alpha + \frac{\pi}{2}\right|}{\frac{2 \cdot \pi}{n}}\right)$$

and $$\alpha \in [0, 2\pi]$$

where $R_0$ represents the maximum distance between the centre of the extrudate and the wall of the extrudate, R represents the distance between the centre of the extrudate and the wall of the extrudate for an angle $\alpha$, r represents the radius of one lobe of the extrudate, and n corresponds to the number of lobes of the extrudate, and the function Int( ) represents the integral part of the ratio $$\left(\frac{\left|\alpha + \frac{\pi}{2}\right|}{\frac{2 \cdot \pi}{n}}\right) \text{ and } \left|\alpha + \frac{\pi}{2}\right|$$

represents the absolute value of the sum $$\alpha + \frac{\pi}{2}.$$

3. A process according to claim 1, in which the extrudate is characterized by a number of lobes n selected from the group constituted by the integral values 3, 4, 5, 6, 7, 8, 9 and 10.

4. A process according to claim 3, in which the extrudate is characterized by a number of lobes n selected from the group constituted by the integral values 3, 4, 5 and 6.

5. A process according to claim 1, in which the length h of the extrudate is in the range 0.5 to 50 mm.

6. A process according to claim 1, in which the extrudate is a supported extrudate comprising a porous support based on gel alumina.

7. A process according to claim 6, in which the porous support is 100% constituted by a gel alumina.

8. A process according to claim 1, in which the active phase contains 1% to 70% by weight of sulphur.

9. A process according to claim 1, in which at least 90% by weight of the active phase is in the form of cuprous copper sulphide, CuS, or in the form of iron sulphide $FeS_2$.

10. A process according to claim 1, in which the extrudates are inscribed in a cylinder with a diameter in the range 0.5 to 100 mm.

11. A process according to claim 1, in which the effluent is at a temperature in the range −50° C. to +200° C., a pressure in the range 1 to 50 MPa and a volume of feed per volume of capture mass per hour in the range 500 to 50000 $h^{-1}$.

12. A process according to claim 1, in which the feed is a gas of industrial origin, a synthesis gas, a natural gas, gas phase condensates or liquid hydrocarbon feeds containing at least heavy metals selected from the group constituted by mercury, arsenic and lead.

13. A process according to claim 1, in which the feed is a gas of industrial origin, a synthesis gas, a natural gas, gas phase condensates or liquid hydrocarbon feeds containing at least mercury.

* * * * *